United States Patent [19]

Grendahl et al.

[11] Patent Number: 5,509,903
[45] Date of Patent: Apr. 23, 1996

[54] SYRINGE HAVING A FLEXIBLE COLLAR

[75] Inventors: Dennis T. Grendahl, 2070 Shoreline Dr., Orono, Minn. 55391; Fritz D. Harnsberger, Santa Barbara, Calif.

[73] Assignee: Dennis T. Grendahl, Orono, Minn.

[21] Appl. No.: 978,812

[22] Filed: Nov. 19, 1992

[51] Int. Cl.[6] .................................................. A61M 5/00
[52] U.S. Cl. ................................. 604/187; 604/227
[58] Field of Search ................................ 604/187, 227, 604/218, 192, 263

[56] References Cited

U.S. PATENT DOCUMENTS

| | | | |
|---|---|---|---|
| D. 249,808 | 10/1978 | Bloom et al. | |
| 2,854,975 | 10/1958 | Cohen | 604/227 |
| 3,316,909 | 5/1967 | Cowley | 604/227 |
| 3,921,633 | 11/1975 | Tischlinger | |
| 3,978,858 | 9/1976 | Tischlinger | |
| 3,987,940 | 10/1976 | Tischlinger | 604/227 X |
| 4,068,661 | 1/1978 | Hennings | 604/227 |
| 4,291,695 | 9/1981 | Bekkering et al. | 604/227 X |
| 4,540,405 | 9/1985 | Miller et al. | |
| 4,909,788 | 3/1990 | Egolf | 604/227 |
| 5,338,309 | 8/1994 | Imbert | 604/227 |

FOREIGN PATENT DOCUMENTS 773091  10/1971  Belgium ........................ 604/227

*Primary Examiner*—John D. Yasko
*Attorney, Agent, or Firm*—Grady J. Frenchick; Stroud, Stroud, Willink, Thompson & Howard

[57] ABSTRACT

The disclosure relates to syringes which include a substantially rigid, hollow syringe body, a plunger and a flexible, finger-conformable grip, guard, collar or collet which are disposed about one end thereof.

9 Claims, 2 Drawing Sheets

SYRINGE HAVING A FLEXIBLE COLLAR

This invention relates to syringes. More particularly, this invention relates to syringes which are particularly adapted to dispensing viscous fluids. Yet more particularly, this invention relates to syringes which include a substantially rigid, hollow syringe body, a plunger, and a flexible, finger-conformable grip, guard, collar, or collet disposed about one end thereof.

DESCRIPTION OF THE PRIOR ART

Syringes with collars or finger grips are known to the art. For example, U.S. Pat. No. 3,987,940 and 3,987,940 both to Edward A. Tischlinger disclose syringes comprising a glass tube having a uniform outer diameter, a thermoplastic finger-grip sleeve and a nose-forming sleeve disposed on opposite ends thereof. Both the finger-grip sleeve and the nose-forming sleeve are cam-stretched onto the glass syringe body. The finger grip sleeve has two oppositely outstanding wing portions which act as finger grips.

U.S. Pat. No. 3,921,633 also to Edward A. Tischlinger discloses a similar structure with an added interior collet which interacts with the finger grip sleeve. Again, the sleeve of the Tischlinger '633 patent has two oppositely disposed wing portions which act as finger grips.

U.S. Pat. No. 4,068,661 to Hennings discloses an injection syringe with a separate one-piece finger rest. The finger rest of Hennings is disclosed to be made of glass or synthetic plastics. The finger rest of Hennings also is shown to be two oppositely disposed wing portions which provide the finger rest area or region.

U.S. Pat. No. 4,909,788 to George Egolf discloses a syringe with an adjustable winged collar. The syringe of Egolf also shows a finger grip comprising diametrically opposite wings. U.S. Pat. No. 3,316,909 to C. C. Cowley and U.S. Pat. No. 2,854,975 to M. J. Cohen both disclose conventional syringes with finger grip structures which are intended to dispense a medicament contained therein using one hand.

None of the above references, alone or in combination disclose or suggest the present invention.

BRIEF SUMMARY OF THE INVENTION

Briefly, in one aspect the present invention is a syringe comprising a substantially rigid cylindrical body, said body having an axis, inner and outer surfaces, a nozzle or attachment end and a plunger or Open end. The plunger end of the syringe body has an outwardly flared flange, the flange having a radial leading surface, and a lip, the leading surface of the flange blending the outer surface of the syringe body with said flange lip. A syringe body of this invention has disposed thereabout, a flexible, conformable finger grip collar, said collar having inner and outer surfaces and being substantially radially symmetric with respect to said axis, said inner surface being concave and being adapted to cooperate with the leading surface of said flange to prevent said body from passing through said collar, the outer surface of said collar defining a continuous multiplicity of radially symmetric facets. The facets prevent the syringe from rolling when the syringe is placed upon a horizontal surface and the collar disposes the axis of the syringe at an angle with respect to a horizontal surface upon which the syringe may be placed. A "radially disposed" or "radially symmetric" facet of this invention is a facet or face or surface in which corresponding portion are disposed equidistant from the axis of the syringe body. For example, the centers and ends of a radially symmetric facet would lie in a circle, the center of which would be the axis of the syringe body.

A completed syringe of this invention includes a syringe plunger having a shank and a head against which a user's finger is placed. The leading or fluid contact end of the shank is adapted to cooperate with the inside surface of the syringe body to eject liquid from its nozzle end. In a preferred embodiment, the plunger shank is hollow. The hollow plunger shank provides a cylindrical space which can be used to store or transport, e.g., a needle or cannula, to be attached to the nozzle end of the syringe body when the syringe is to be used. In another preferred embodiment, the head comprises a finger flange or rim which defines a concave finger-contacting surface. In a most preferred embodiment of the plunger structure of this invention, the concave surface of the syringe head leads to the hollow interior of the plunger.

In one embodiment of the present invention, the outer surface of the finger grip defines 6 substantially radially symmetric facets. In a second embodiment of the present invention, the outer surface of the flange defines 8 radially facets.

The finger grip of this invention is said to be "conformable" or flexible. By this it is meant that the material of which the finger grip is made conforms or complies with fingers placed therearound so as to provide a soft or flexible feel or tactility. Generally speaking, a material which is sufficiently conformable to be useable in this invention will have a Shor A durometer value which is less than about 90. Preferably, a conformable material useable for the collar of the present invention will have a Shor A durometer reading in the range of about 45 to 90, preferably about 60 to about 80. The material commercially available under the trade designation "C-Flex" is a preferred conformable material from which the present collar may be fabricated.

A syringe of the present invention is particularly adapted for dispensing viscous fluids. By "viscous" herein it is meant a fluid having a viscosity in the range of about 3,000 to 60,000 cps, preferably about 10,000 to about 25,000 cps. For example, during various ophthalmic surgical procedures a viscous fluid (sometimes referred to a viscous adduct) is dispensed to the surgical cite for lubrication and reduction of surgical trauma. A syringe of the present invention is particular adapted for dispensing such viscous fluids because, being conformable, it adapts to the user's fingers during the dispensing operation. This is significant because dispensing of viscous fluids requires greater injection force than dispensing water-like drugs or drug solutions.

A syringe of the present also has the advantage of having a reduced tendency to roll when placed upon a horizontal surface. This also is a significant aspect of the invention because during the above-described ophthalmic surgical procedures it may be necessary to employ the syringe carrying the viscous fluid a number of times as the surgery progresses. Between these usage events, the syringe-carrier may be set aside. The multi-faceted collar means that essentially no matter what position the syringe is placed in the surgical arena (e.g., on a surgical table), it will not roll and will be readily available to the surgeon when its retrieval is desired.

Moreover, the collar requires that the axis of the syringe be obliquely or angularly disposed with respect to a horizontal surface. This angular placement causes any liquid within the syringe to flow toward its tip end. This angular configuration also makes the syringe easier to pick up since the physician's fingers can easily be slid between the barrel of the syringe and the top of the instrument table on which the syringe rests. To applicant's knowledge, these and other advantages of the present invention are unknown to syringes of the prior art.

BRIEF DESCRIPTION OF THE DRAWINGS

The present invention will now be described by reference to the following detailed description of the invention and by reference to the Figures in which like numerals are used to refer to like features in the various embodiments and in which.

DETAILED DESCRIPTION OF THE INVENTION

Figure 1:
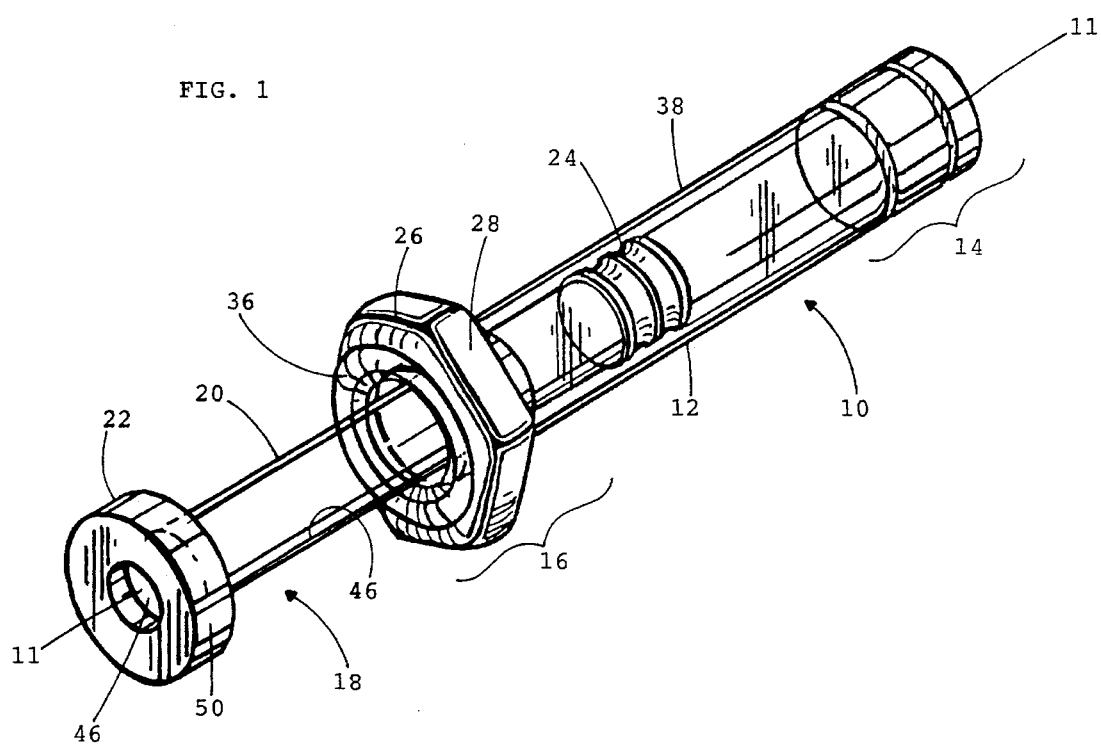
FIG. 1 is a perspective view of a syringe of the present invention.
Figure 2:
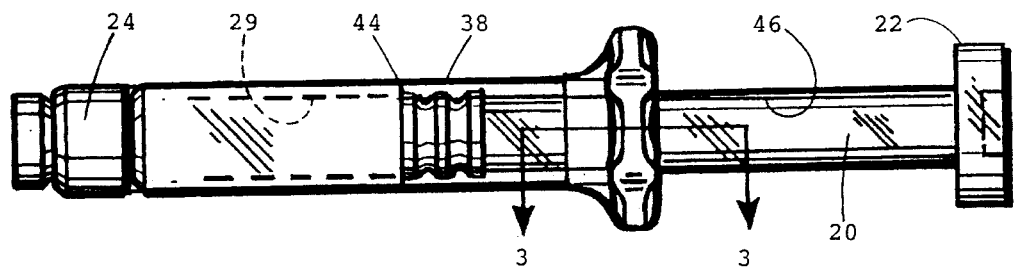
FIG. 2 is a side elevational view of the syringe shown in FIG. 1.
Figure 3:
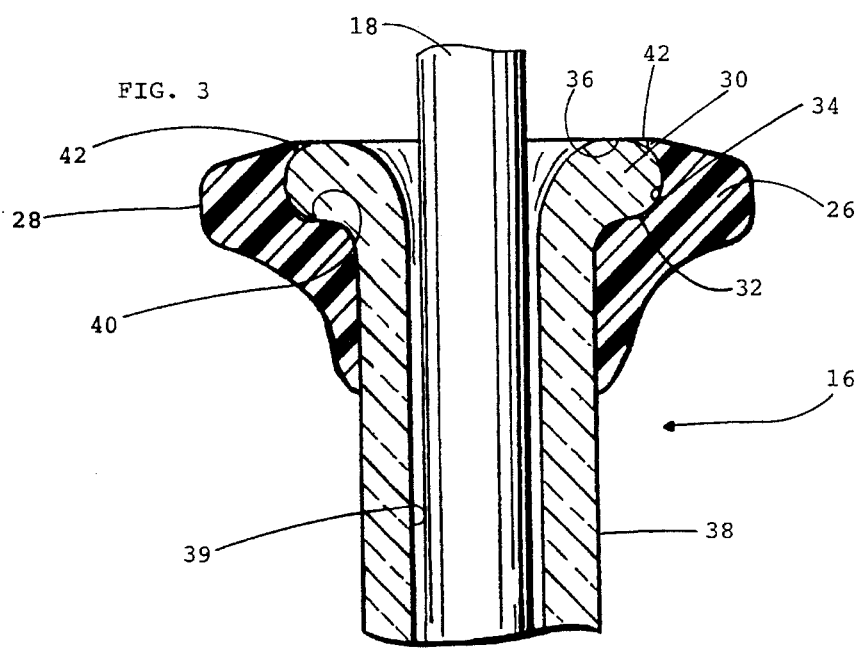
FIG. 3 is a section of the plunger end of the embodiment of the invention shown in FIG. 1 taken along line 3—3 of FIG. 2 and rotated 90 degrees counter clockwise.

Thus there is shown in the FIG. 1-3 a syringe 10. Syringe 10 has an axis 11 and comprises a substantially rigid, hollow cylindrical syringe body or barrel 12. Syringe body 12 has an exterior surface 38 and an interior surface or bore 39. Barrel 12 has a substantially closed or restricted nozzle end 14 and an open or plunger end 16. Nozzle end 14 of syringe 10 can be of any particular configuration depending upon the application for which the syringe is to be used. Usually a Luer connector or coupler would be employed to couple the nozzle end of the syringe body with e.g., a cannula or a needle. As also is shown in FIG. 1 syringe 10 includes a plunger 18 comprising a plunger shank 20 and a plunger head 22. Plunger head 22 comprises a finger flange or rim 50. Plunger head 22 may be flat (as shown) or preferably is concave or recessed. Plunger 18 is hollow having an elongate cavity 48 defined by the inside wall thereof.

Plunger 18 employs a gasket 24 disposed about plunger shank leading or distal end to provide a frictional, sliding, fluid-restrictive fit between the plunger shank 20 and the inside wall or surface 39 of syringe body 12. By moving plunger 18 within syringe body 12 from the plunger end to the nozzle end (generally in a left to right direction in FIG. 1), fluid within syringe body 12 is delivered or expelled from nozzle end 14.

Radially disposed around or about plunger end 16 of syringe body 12 is conformable finger guard or collar 26° While the details of collar 26 are more completely discussed below, in the embodiment of FIG. 1 finger guard 26 has 6 facets which are symmetrically radially disposed about the axis 11 of the syringe 10.

FIG. 2 shows a side elevational view of the syringe of FIG. 1. In this view, the nozzle end of syringe 10 has a cap 24. Various other nozzle end configurations could be employed, depending upon the application for the syringe and upon the liquid to be dispensed therefrom. FIG. 2 shows in phantom (at 29) the path that would be subtended by the edge 44 of the outer rim of gasket 24 if plunger 18 were moved from a first position as shown in FIG. 2 to a second position with gasket 20 substantially adjacent nozzle end 14. In this maneuver, material within the syringe would be expelled or delivered to the surgical site.

Referring to FIG. 3, it is seen that plunger end 16 of syringe body 12 is outwardly flared. Outward flare 30 has a radial leading surface 32, a curved edge 34, and a following interior surface 36. Flange leading surface 32 generally merges outside surface 38 of barrel 12 into flange edge 34. Flange leading surface 32 is generally perpendicular to the axis of syringe 10. Finger grip or collar 26 is disposed about and around outward flare 30 and substantially enshrouds it.

Cooperating with flange leading surface 32 is finger grip interior concave surface 40. Surface 36 and surface 40 cooperate with one another so that finger grip 26 is frictionally engaged around syringe body 12 and prevents syringe body 12 from passing therethrough as plunger 18 passes into the syringe. Finger grip 26 can be "snapped" into place and held about syringe edge 34 by radial rim or lip 42. Because the collar is conformable, lip 42 can easily be molded to flex forward as the syringe body is assembled by passing it through the collar and snapping into place behind the flange as surfaces 36 and 40 mate. Alternatively, rim 42 could be eliminated and, for example, an adhesive used at the surface interface(s) between the syringe flange and finger grip 26.

Figure 4:
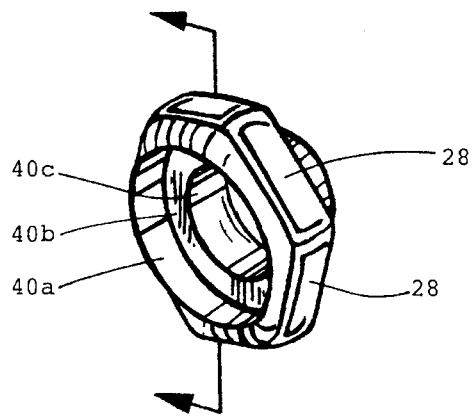
FIG. 4 is a perspective view of a finger guard or collar of the present invention.

FIG. 4 shows a perspective view of the conformable finger grip or collar 26 of this invention. Of particular note are facets or flats 28 which define the outermost perimeter of the collar. The concave interior of grip 26 is shown to comprise a first radial surface 40' of a first larger diameter, an orthogonal surface 40" (with respect to the axis of the grip and the syringe) and a second radial surface 40"' having a second smaller diameter. Second radial surface 40"' fits restrictively around the outer surface 38 of syringe barrel 12 while first radial surface 40' fits generally around and over flange edge 34. Orthogonal surface 40" blends between surfaces 40' and 40"' to complete the definition of concave surface 40. Orthogonal surface 40" also cooperates with flange leading surface 32 when the syringe and finger grip are assembled.

Figure 5:
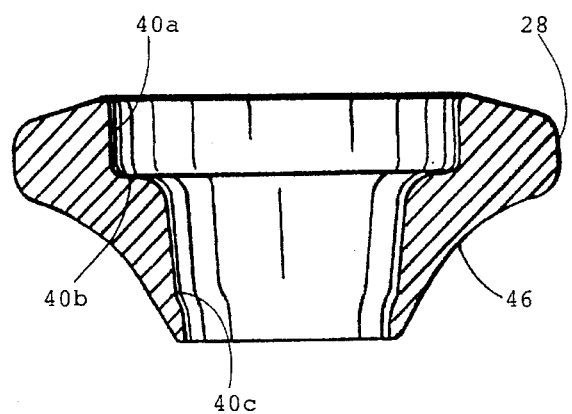
FIG. 5 is a sectional view of the finger guard shown in FIG. 4 taken along line 5—5 of FIG. 4.
Figure 6:
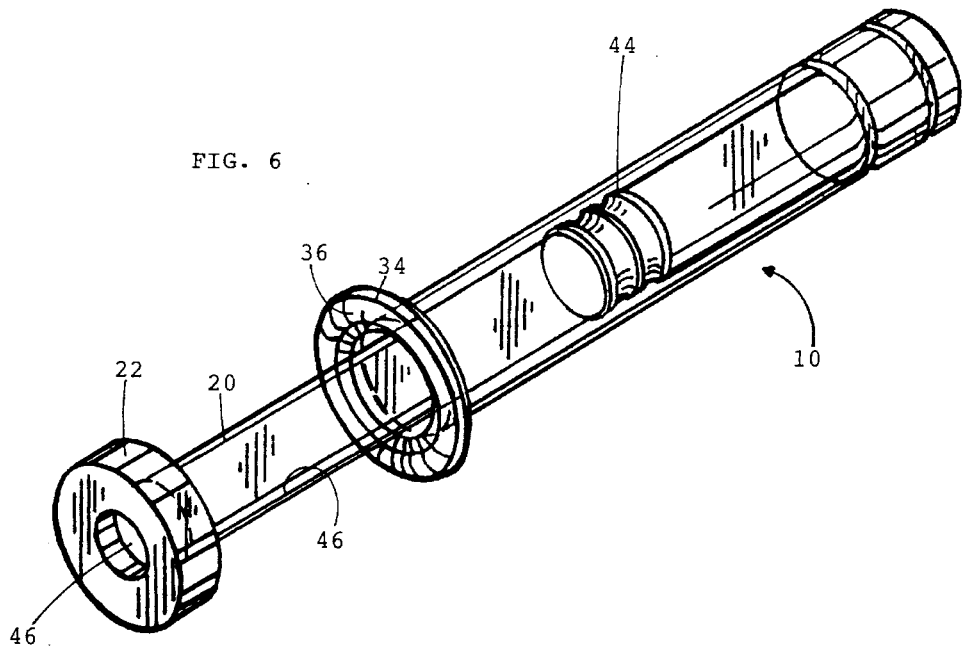
FIG. 6 is an elevational view of the embodiment of the invention shown in FIG. 1 with the finger collar removed.

FIG. 5 shows a sectional view of the syringe collar of FIG. 4 taken along line 5—5 of FIG. 4. FIG. 5 illustrates the embodiment of the invention discussed above in which lip or following rim 42 has been deleted from the structure. A collar of FIG. 5 would not affirmatively snap into place around the plunger end of a syringe because the omitted lip would not be biased forward during assembly of the syringe only to snap behind the flared end of the syringe, once the syringe had passed therethrough. Optionally, a suitable adhesive could be used on surfaces 40', 40", or 40 "' to aggressively adhere the collar to the syringe body.

One skilled in this art will readily appreciate how the present invention is used to dispense fluids from the syringe. Basically, the user would place his or her first and second fingers around or adjacent collar outside surface 46, his or her thumb behind plunger 18 and move plunger 18 from its first position (as shown in FIG. 2) to its second position (as described above). In this manner, liquid within the syringe would be dispensed or expelled from nozzle end 14.

The present syringe provides a further advantage in that it is operable with one hand. This is important because in many surgical procedures, the nurse or physician may not have both hands available to manipulate a syringe. This invention, with its flexible finger guard permits one-hand dispensing of liquids from with the syringe. The present syringe also does not require excessively an excessively larger package (e.g., for shipment). This can be an important advantage over known three ring syringes. Coupled with its other advantages of not rolling on horizontal surfaces and being easy to pick up, especially with a gloved hand, it is seen that the present invention provides significant, important advantages over syringes known to the prior art.

The finger guard or collar of this invention comprises a syringe body and a conformable collar. The syringe body may be comprised of any substantially rigid material. Substantially rigid thermosetting or thermoplastic materials may be used to form or mold the syringe body. Alternatively, a frangible materials such as glass or ceramics also may be used. The guard to some extent protects the syringe body from breakage thus permitting a wide range of materials to be employed.

What is claimed is as follows:

1. A syringe comprising:

a plunger, a substantially rigid cylindrical body, said body having an axis, an outer surface and an inner surface, a nozzle end, and a plunger end, the plunger end having an outwardly flared flange, the flange having a radial leading surface, and a lip, the leading surface of the flange blending the outer surface of the syringe body with said flange lip, the plunger end the syringe body having disposed thereabout, a flexible, conformable finger grip collar, said collar having inner and outer surfaces and being substantially radially symmetric with respect to said axis, said inner surface being concave and being adapted to cooperate with the leading surface of said flange to prevent said body from passing through said collar, the outer surface of said collar defining a continuous multiplicity of radially disposed facets and a finger contacting surface, said facets being substantially flat whereby the facets prevent the syringe from rolling when the syringe is placed upon a horizontal surface and the collar disposes the axis of the syringe at an angle with respect to a horizontal surface upon which the syringe may be placed.

2. A syringe according to claim 1 wherein the collar has 6 facets.

3. A syringe according to claim 1 wherein the collar has 8 facets.

4. A syringe according to claim 1 wherein the collar has a Shor A durometer value of about 45 to about 90.

5. A syringe according to claim 1 wherein the collar has a durometer value of about 60 to about 80.

6. A syringe according to claim 1 wherein the concave interior surface of the collar comprises a radial neck surface having a first diameter, the neck surface merging to define an orthogonal surface the plane of which is substantially perpendicular to the axis of the syringe, the orthogonal surface merging to a second radial surface having a second diameter which is larger than the diameter of the neck surface.

7. A syringe according to claim 6 wherein the second radial surface includes an outwardly disposed following lip.

8. A syringe according to claim 1 wherein the plunger is hollow.

9. A syringe according to claim 1 wherein the plunger comprises a concave radial flange which communicates with an interior hollow bore.

* * * * *

UNITED STATES PATENT AND TRADEMARK OFFICE
CERTIFICATE OF CORRECTION

PATENT NO.  : 5,509,903
DATED       : April 23, 1996
INVENTOR(S) : Dennis T. Grendahl et al.

It is certified that error appears in the above-indentified patent and that said Letters Patent is hereby corrected as shown below:

Column 4, line 31, "40'" should read --40a--.

Column 4, line 32, "40''" should read --40b--.

Column 4, lines 33 and 34, "40'''" should read --40c--.

Column 4, line 36, "40'" should read --40a--.

Column 4, line 37, "40''" should read --40b--.

Column 4, line 38, "40'" should read --40a--.

Column 4, line 38, "40'''" should read --40c--.

Column 4, line 39, "40''" should read --40b--.

Column 4, line 51, "40'" should read --40a--.

Column 4, line 51, "40''" should read --40b--.

Column 4, line 51, "40'''" should read --40c--.

Signed and Sealed this

Fifth Day of August, 1997

Attest:

Attesting Officer

BRUCE LEHMAN

Commissioner of Patents and Trademarks